United States Patent
Padilla et al.

(10) Patent No.: US 12,161,817 B2
(45) Date of Patent: *Dec. 10, 2024

(54) CATHETER WITH IMPROVED LOOP CONTRACTION AND GREATER CONTRACTION DISPLACEMENT

(71) Applicant: BIOSENSE WEBSTER (ISRAEL) LTD., Yokneam (IL)

(72) Inventors: Ricardo Padilla, Tustin, CA (US); Homero Padilla, Rancho Cucamonga, CA (US); Julie Bui, Rosemead, CA (US); Mario Solis, Rancho Cucamonga, CA (US); Thomas Selkee, Claremont, CA (US); Jose Jimenez, Ontario, CA (US); Keshava Datta, Chino Hills, CA (US); Fernando Salazar, Pomona, CA (US)

(73) Assignee: BIOSENSE WEBSTER (ISRAEL), LTD., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/469,535

(22) Filed: Sep. 18, 2023

(65) Prior Publication Data

US 2024/0001081 A1 Jan. 4, 2024

Related U.S. Application Data

(63) Continuation of application No. 17/174,135, filed on Feb. 11, 2021, now Pat. No. 11,872,358, which is a
(Continued)

(51) Int. Cl.
*A61B 18/14* (2006.01)
*A61B 5/00* (2006.01)
(Continued)

(52) U.S. Cl.
CPC ......... *A61M 25/0147* (2013.01); *A61B 5/287* (2021.01); *A61B 5/6857* (2013.01);
(Continued)

(58) Field of Classification Search
CPC ............ A61M 25/0147; A61M 25/005; A61M 2025/015; A61M 2205/0266;
(Continued)

(56) References Cited

U.S. PATENT DOCUMENTS 5,820,591 A  10/1998  Thompson et al.
6,064,902 A  5/2000  Haissaguerre et al.
(Continued)

FOREIGN PATENT DOCUMENTS

CN  102846374 A  1/2013
CN  103099675 A  5/2013
(Continued)

OTHER PUBLICATIONS

Extended European Search Report for European Patent Application No. 18163911, mailed on Jun. 15, 2018, 6 pages.
(Continued)

*Primary Examiner* — Adam Z Minchella
(74) *Attorney, Agent, or Firm* — Calderon Safran & Wright P.C.; Etan S. Chatlynne

(57) ABSTRACT

A catheter with a variable circular loop is responsive to a contraction wire for increasing the coiling of the circular loop. The shape of the loop is supported by an elongated member, wherein a radially constrictive sleeve confines the contraction wire to extends immediately alongside the length of elongated member so as to improve uniformity and minimize misshaping of the loop during contraction.

19 Claims, 10 Drawing Sheets

Related U.S. Application Data continuation of application No. 15/470,291, filed on Mar. 27, 2017, now Pat. No. 10,918,832.

(51) Int. Cl.
  *A61B 5/287* (2021.01)
  *A61M 25/00* (2006.01)
  *A61M 25/01* (2006.01)
  *A61B 17/00* (2006.01)
  *A61B 18/00* (2006.01)

(52) U.S. Cl.
  CPC ....... *A61B 18/1492* (2013.01); *A61M 25/005* (2013.01); *A61B 2017/00318* (2013.01); *A61B 2018/00196* (2013.01); *A61B 2018/00375* (2013.01); *A61B 2018/00577* (2013.01); *A61B 2018/00839* (2013.01); *A61B 2018/1435* (2013.01); *A61B 2218/002* (2013.01); *A61B 2562/0209* (2013.01); *A61B 2562/043* (2013.01); *A61M 2025/015* (2013.01); *A61M 2205/0266* (2013.01)

(58) Field of Classification Search
  CPC . A61B 5/0422; A61B 5/6857; A61B 18/1492; A61B 2017/00318; A61B 2018/00196; A61B 2018/00375; A61B 2018/00577; A61B 2018/00839; A61B 2018/1435; A61B 2218/002; A61B 2562/0209; A61B 2562/043
  See application file for complete search history.

(56) References Cited

U.S. PATENT DOCUMENTS

| | | | |
|---|---|---|---|
| 6,071,274 A | 6/2000 | Thompson et al. | |
| 6,468,260 B1 | 10/2002 | Bumbalough et al. | |
| 6,500,167 B1 | 12/2002 | Webster, Jr. | |
| 6,522,933 B2 | 2/2003 | Nguyen | |
| 6,973,339 B2 | 12/2005 | Govari | |
| 7,008,401 B2 | 3/2006 | Thompson et al. | |
| 8,608,735 B2 | 12/2013 | Govari et al. | |
| 8,792,962 B2 | 7/2014 | Esguerra et al. | |
| 2001/0020174 A1 | 9/2001 | Koblish | |
| 2001/0027310 A1 | 10/2001 | Parisi et al. | |
| 2003/0014037 A1 | 1/2003 | Thompson et al. | |
| 2003/0105453 A1* | 6/2003 | Stewart ............. | B29C 66/12445 604/537 |
| 2004/0116848 A1* | 6/2004 | Gardeski ........... | A61M 25/0152 604/95.01 |
| 2004/0181208 A1* | 9/2004 | Poole ................. | A61L 29/02 604/527 |
| 2005/0010095 A1 | 1/2005 | Stewart et al. | |
| 2007/0270679 A1 | 11/2007 | Nguyen et al. | |
| 2012/0116382 A1* | 5/2012 | Ku ..................... | A61M 25/0147 606/33 |
| 2012/0172703 A1 | 7/2012 | Esguerra et al. | |
| 2013/0006238 A1* | 1/2013 | Ditter ................ | A61B 18/1492 606/41 |
| 2013/0338467 A1* | 12/2013 | Grasse .............. | A61B 18/1492 606/41 |
| 2014/0135686 A1 | 5/2014 | Jimenez et al. | |
| 2014/0276745 A1 | 9/2014 | Goshayeshgar et al. | |
| 2014/0276779 A1 | 9/2014 | Grunewald | |
| 2016/0128771 A1 | 5/2016 | Ditter et al. | |
| 2018/0078738 A1* | 3/2018 | Yazdanpanah .... | A61M 25/0009 |

FOREIGN PATENT DOCUMENTS

| | | |
|---|---|---|
| CN | 105615993 A | 6/2016 |
| CN | 104042332 B | 6/2018 |
| EP | 0766533 A1 | 4/1997 |
| EP | 0895789 A1 | 2/1999 |
| EP | 2540245 A1 | 1/2013 |
| EP | 2609886 A2 | 7/2013 |
| EP | 2979721 A1 | 2/2016 |
| EP | 3034025 A1 | 6/2016 |
| EP | 3342364 A2 | 7/2018 |
| JP | 2002501769 A | 1/2002 |
| JP | 2004275767 A | 10/2004 |
| JP | 2013013726 A | 1/2013 |
| JP | 2014097391 A | 5/2014 |
| WO | 9906095 A2 | 2/1999 |
| WO | 02083017 A1 | 10/2002 |
| WO | 2005094665 A2 | 10/2005 |
| WO | 2006115683 A1 | 11/2006 |

OTHER PUBLICATIONS

Extended European Search Report for European Application No. EP17210699, mailed on Jul. 19, 2018, 11 pages.

Extended European Search Report for European Application No. EP20151234, mailed on Apr. 29, 2020, 8 pages.

Partial European Search Report for European Application No. EP17210699, mailed on Apr. 11, 2018, 12 pages.

* cited by examiner

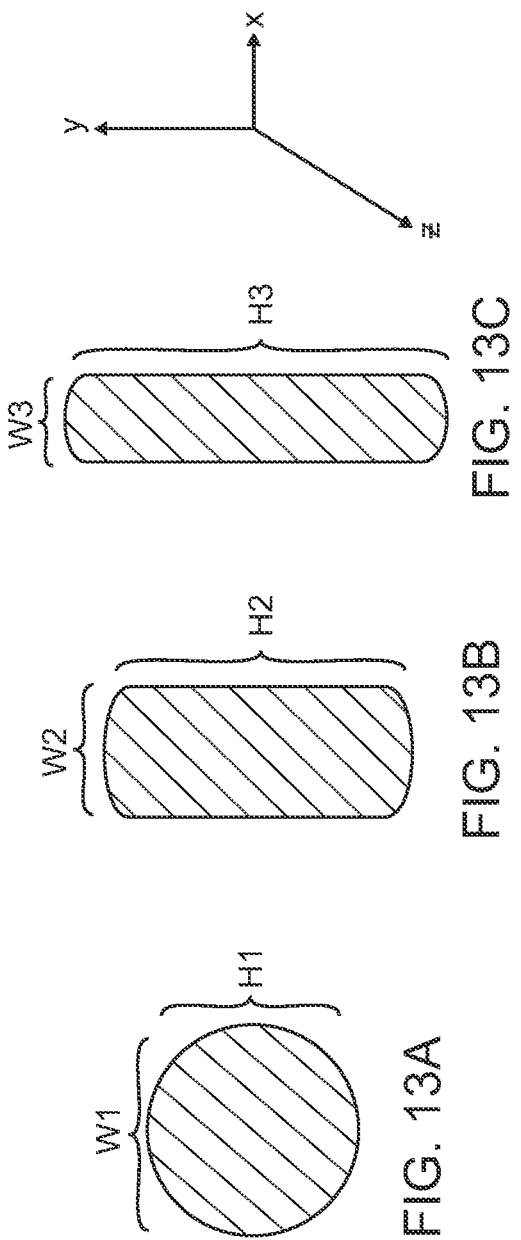

CATHETER WITH IMPROVED LOOP CONTRACTION AND GREATER CONTRACTION DISPLACEMENT

CROSS-REFERENCE TO CO-PENDING APPLICATION

The present application is a Continuation Application under 35 U.S.C. § 120 of U.S. patent application Ser. No. 17/174,135, filed Feb. 11, 2021, which is a Continuation Application under 35 U.S.C. § 120 of U.S. patent application Ser. No. 15/470,291, filed Mar. 27, 2017, now U.S. Pat. No. 10,918,832. The entire contents of these applications are incorporated by reference herein in their entirety.

FIELD OF INVENTION

This invention relates generally to methods and devices for invasive medical treatment, and specifically to catheters, in particular, catheters having distal sections adapted for mapping and ablating selected anatomy.

BACKGROUND

Ablation of myocardial tissue is well known as a treatment for cardiac arrhythmias. In radio-frequency (RF) ablation, for example, a catheter is inserted into the heart and brought into contact with tissue at a target location. RF energy is then applied through an electrode on the catheter in order to create a lesion for the purpose of breaking arrhythmogenic current paths in the tissue.

Circumferential ablation of the ostia of the pulmonary vein is now accepted as a treatment for atrial arrhythmias, and particularly for atrial fibrillation. For example, U.S. Pat. No. 6,064,902, whose disclosure is incorporated herein by reference, describes a catheter for ablating tissue on the inner wall of a blood vessel, such as a pulmonary vein. The tip portion of the catheter is deflectable from a first, generally straight, configuration, in which the proximal and distal sections are substantially co-linear, to a second, J-shaped, configuration in which the proximal and distal sections are generally parallel with a separation therebetween substantially corresponding to the inside diameter of the blood vessel. The distal end portion of the catheter is rotated about the longitudinal axis of the catheter to cause a circumferential displacement of proximal and distal ablation electrodes on the catheter along the inner wall of the pulmonary vein. In this way, the electrode catheter may be used to ablate a number of circumferentially-spaced sites on the inner wall of the pulmonary vein by ablating one or two sites at each circumferential position.

U.S. Pat. No. 6,973,339, whose disclosure is incorporated herein by reference, describes a lasso for pulmonary vein mapping and ablation. A catheter for circumferentially mapping a pulmonary vein (PV) includes a curved section shaped to generally conform to the shape of the interior surface of the PV. The curved section is connected to catheter by a generally straight axial base section that is in an "on edge" configuration where the base axial section connects to the curved section on the circumference of the curved section. The curved section comprises one or more sensing electrodes, and its proximal end is joined at a fixed or generally known angle to a base section of the catheter. Position sensors are fixed to the curved section of the catheter and to the distal end of the base section. The catheter is inserted into the heart, and the curved section is positioned in contact with the wall of the PV, while the base section remains within the left atrium, typically positioned such that the joint with the curved section is at the ostium of the vein. The information generated by the three position sensors is used to calculate the locations and orientations of the sensing electrodes, which enables mapping of the surface of the PV. The sensing electrodes may additionally perform ablation of selected sites, or the catheter may further comprise ablation elements.

U.S. Pat. No. 7,008,401, whose disclosure is incorporated herein by reference, describes compound steering assemblies, usable in both diagnostic and therapeutic applications, for steering the distal section of a catheter in multiple planes or complex curves. These assemblies are said to enable a physician to swiftly and accurately position and maintain ablation and/or mapping electrodes in intimate contact with an interior body surface. U.S. Pat. No. 5,820,591, whose disclosure is incorporated herein by reference, similarly describes compound steering assemblies of this sort.

U.S. Pat. No. 8,608,735 whose disclosure is incorporated herein by reference, describes a medical device, including an insertion shaft, having a longitudinal axis and having a distal end adapted for insertion into a body of a patient. A resilient end section is fixed to the distal end of the insertion shaft and is formed so as to define, when unconstrained, an arc oriented obliquely relative to the axis and having a center of curvature on the axis. One or more electrodes are disposed at respective locations along the end section.

However, because human anatomy varies between individuals, the shape and size of an ostium vary, and the arcuate distal section may not always fit the particular target ostium. Moreover, it may be desirable to use the same catheter for a target ostium of a certain diameter and also the PV of that ostium which may have a significantly lesser diameter. Additionally, where a lasso catheter may have a variable arcuate distal assembly, contraction of the arcuate distal assembly may misshapen the generally circular form of the arcuate distal assembly because one or more of the components thereof are too stiff for tighter coiling in a desirable manner.

Current circular loop catheters are constructed utilizing a support member, e.g., a nitinol spine, with a constant uniform cross-section that fails to consistently maintain a circular configuration during loop contraction. Such current circular loop catheters also are limited in its contraction and deflection characteristics in requiring more pound contraction wire tensile force for less loop contraction. Moreover, current circular loop catheters may lack reliable attachment between the contraction wire and the support member that would eliminate possible breakage or release of the contraction wire from the support member. Current circular loop catheters have nitinol spines with the same uniform area moments of inertia along their entire length and the nitinol spines have the same cross-sectional area.

SUMMARY OF THE INVENTION

The present invention is directed to a catheter having a variable arcuate distal with improved contraction and bending radius characteristics, along with greater durability. The variable arcuate distal section includes a shape-memory support member, a contraction wire, and a radially-constrictive tubing or sleeve to greatly increase the degree of contraction of a generally circular catheter loop while decreasing the forces on the contraction wire and all other structural support portions of the loop and providing operators of the catheter with a repeatable and more truthful round contraction for circular diagnostic and therapeutic catheters.

In some embodiments, the radially-constrictive tubing is transparent or at least translucent so that the contraction wire under the tubing is visible, especially during assembly of the variable arcuate distal section.

In some embodiments, the radially-constrictive tubing has a braided construction so that its radial constriction is increased when tension is applied to the tubing in a longitudinal direction.

In some embodiments, the radially-constrictive tubing is constructed of a manufactured fiber, spun from a liquid crystal polymer (LCP), for example, manufactured fiber sold under the trademark VECTRAN®, created by Celanese Acetate LLC and now manufactured by Kuraray Co., Ltd.

In some embodiments, an electrophysiology catheter includes an elongated catheter body, a contraction wire, and a distal assembly configured for contraction by actuation of the contraction wire. The distal assembly has a shape-memory support member having a 3-D configuration with a distal portion defined by a distal radius.

In more detailed embodiments, the support member has an inner side facing an inner circumference of the 3-D configuration, wherein a coextensive portion of the contraction wire extending through the distal assembly is aligned with the inner side.

In some detailed embodiments, the distal assembly includes a radially constrictive tubing surrounding the support member and a coextensive portion of the contraction wire with the support member.

In some detailed embodiments, the support member and the coextensive segment of the contraction wire jointly define a cross-sectional profile, and the radially constrictive tubing surrounds the support member and the coextensive segment generally in conformity to the cross-sectional profile.

In some detailed embodiments, the coextensive portion of the contraction wire is aligned with a flat side of the support member and configured to maintain the coextensive segment of the contraction wire generally in align the flat side during contraction of the distal assembly.

In some embodiments, an electrophysiology catheter has an elongated catheter body defining a longitudinal axis, a contraction wire, and a 3-D distal assembly movable between a neutral configuration and a contracted configuration in response to longitudinal movement of the contraction wire. The 3-D distal assembly has at least an elbow defined by a proximal diameter and a distal portion defined by a distal diameter, and a radially constrictive tubing that extends generally between the elbow junction and the distal portion. For the neutral configuration, the proximal diameter is less than the distal diameter. For the contracted configuration, the distal diameter is about equal to or less than the proximal diameter.

In some detailed embodiments, the elbow junction has a twist configured to support the distal portion generally transversal to the longitudinal axis such that the longitudinal axis extends through a center of the distal portion.

In some detailed embodiments, the distal assembly has an elongated support member having an inner flat side and an opposing flat side, and wherein the contraction wire has a distal segment coextensive with the inner flat side along its entire length.

In some detailed embodiments, the inner side of the support member is on or near an inner circumference of the distal portion of the 3-D distal assembly.

In some embodiments, the distal assembly further includes a radially-constrictive tubing circumferentially surrounding at least a portion of the elongated support member and a friction-reducing tubing surrounding a portion of the contraction wire.

In some embodiments, the radially-constrictive tubing is circumferentially constrictive around the support member and the friction-reducing tubing in minimizing lateral movement of the contraction wire relative to the support member.

In other embodiments, an electrophysiology catheter has an elongated catheter body defining a longitudinal axis, a contraction wire, and a distal assembly with a 3-D arcuate form, the distal assembly movable between a neutral configuration and a contracted configuration in response to longitudinal movement of the contraction wire. The distal assembly has a support member providing the 3-D arcuate form, the 3-D arcuate form having an elbow junction and a distal portion, the elbow junction defined by at least a proximal diameter and the distal portion defined by a distal diameter, and a radially constrictive tubing surrounding the support member and a coextensive portion of the contraction wire. For the neutral configuration, the proximal diameter is less than the distal diameter. For the contracted configuration, the distal diameter is decreased to a diameter about less than the distal diameter.

In some detailed embodiments, the 3-D arcuate form defines an inner circumference, the distal assembly includes a tubing with multiple lumens including a lumen closest to the inner circumference, and the support member and the coextensive portion of contraction wire are in the lumen closest to the inner circumference.

In some detailed embodiments, the support member has a generally-rectangular cross-section, the support member having a distal portion wherein a width dimension and a height dimension of the generally rectangular cross-section varies along the length of the distal portion.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 13A is an end cross-sectional view of the support member of FIG. 6A, before reshaping.

FIG. 13B is an end cross-sectional view of the support member of FIG. 6A, taken along line G-G.

FIG. 13C is an end cross-sectional view of the support member of FIG. 6A, taken along line J-J.

DETAILED DESCRIPTION OF THE INVENTION

Embodiments of the present invention that are described hereinbelow provide probes, such as catheters, with improved arcuate distal electrode-carrying structures, to facilitate maneuvering and positioning in the heart and especially tubular regions of different sizes in a patient's body and different circumferential locations within the tubular regions. Such catheters can be used to produce generally circular or helical ablation paths, as well as sensing electrical activity along a generally curve or helical pattern for electrical potential and anatomical mapping.

Figure 1:
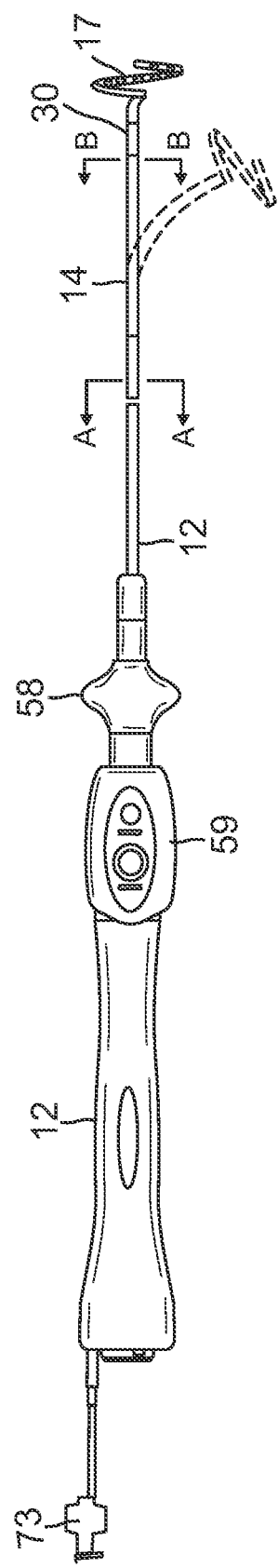
FIG. 1 is a top plan view of a catheter of the present invention, according to one embodiment.
Figure 2B:
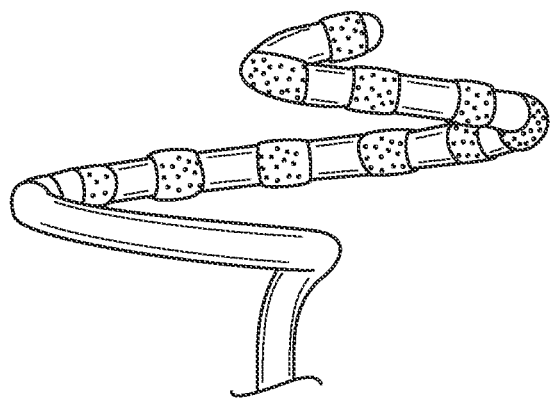
FIG. 2B is the detailed view of the 3-D arcuate distal assembly of FIG. 2, in a contracted configuration.
Figure 2A:
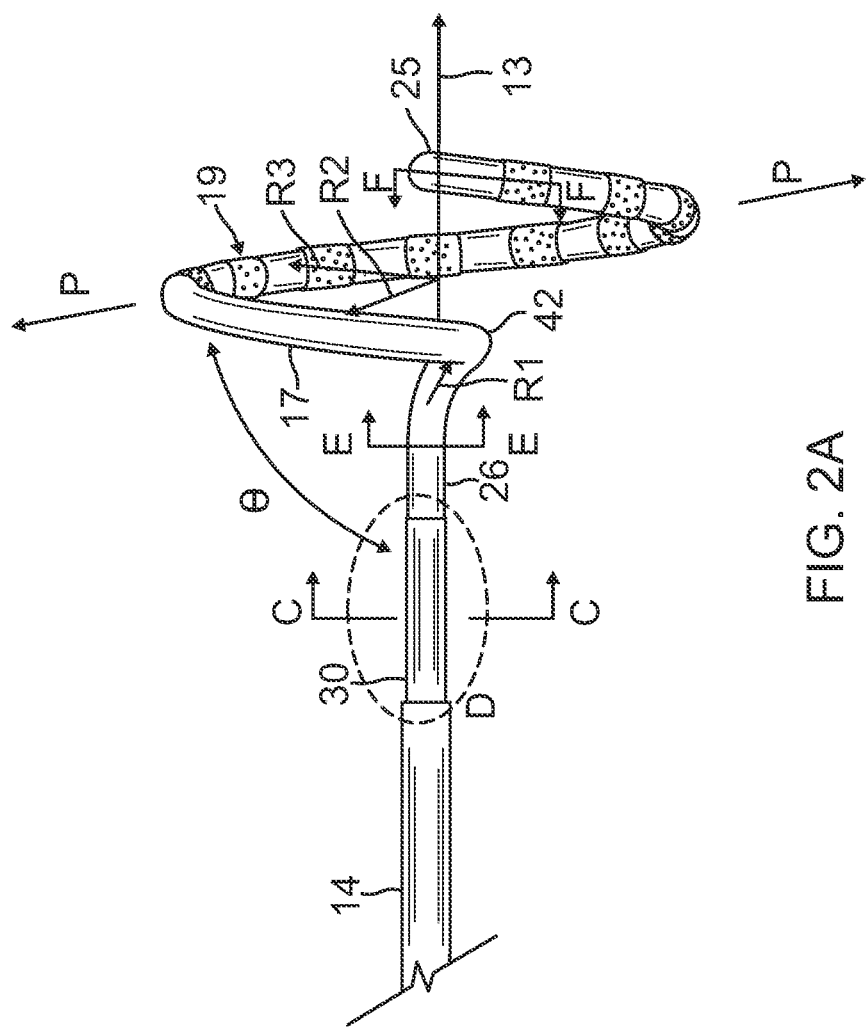
FIG. 2A is a detailed view of a 3-D arcuate distal assembly of the catheter of FIG. 1, in a neutral, unconstrained configuration.

Referring to FIG. 1, a catheter 10 according to the disclosed embodiments comprises an elongated body that may include a flexible insertion shaft or catheter body 12 having a longitudinal axis 13, and an intermediate section 14 distal of the catheter body that can be uni- or bi-directionally deflected off-axis from the longitudinal axis 13. As shown in FIG. 2A, extending from the intermediate section 14 is a resilient three-dimensional (3-D) arcuate distal assembly 17 which is advantageously constructed for significantly greater and more uniform loop contraction. As explained below in further detail, the distal assembly 17 is responsive to operator manipulation of a control handle 16 in decreasing its radius and increasing its coiling, as shown in FIG. 2B.

Figure 3:
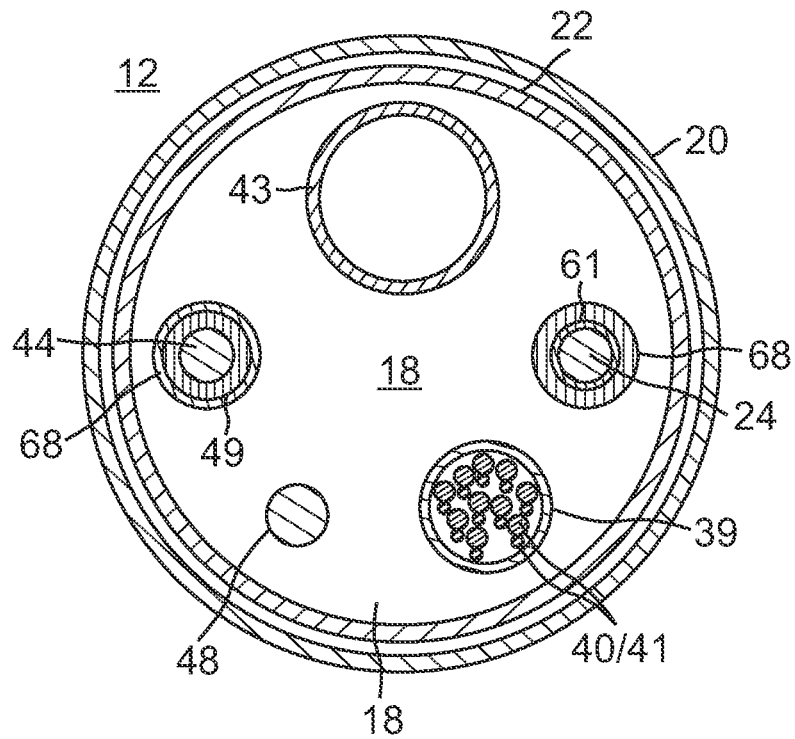
FIG. 3 is an end cross-sectional view of a catheter body of the catheter of FIG. 1, taken along line A-A.

In the depicted embodiment of FIG. 1 and FIG. 3, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. In some embodiments, the construction comprises an outer wall 20 made of polyurethane or PEBAX. The outer wall 20 comprises an imbedded braided mesh of stainless steel or the like, as is generally known in the art, to increase torsional stiffness of the catheter body 12 so that, when the control handle 16 is rotated, the intermediate section 14 will rotate in a corresponding manner.

The outer diameter of the catheter body 12 is not critical, but in some embodiments is no more than about 8 french, more preferably 7 french. Likewise the thickness of the outer wall 20 is not critical, but is thin enough so that the central lumen 18 can accommodate any desired wires, cables and/or tubes. The inner surface of the outer wall 20 is lined with a stiffening tube 22 to provide improved torsional stability. The outer diameter of the stiffening tube 22 is about the same as or slightly smaller than the inner diameter of the outer wall 20. The stiffening tube 22 can be made of any suitable material, such as polyimide, which provides very good stiffness and does not soften at body temperature.

The deflectable intermediate section 14 comprises a shorter section of tubing 23 having multiple lumens, most of which are occupied by the various components passing from the catheter 12 and into the intermediate section 14. In the illustrated embodiment of FIG. 4, there are six lumens. Coupled to the ring electrodes 19, respective lead wire/thermocouple pairs 40, 41 pass through a first lumen 31. A nonconductive protective sheath 39 may be provided to surround the wire pairs 40/41. An irrigation tubing 43 for delivering irrigation fluid to the distal assembly 17 passes through a second lumen 32. For enabling deflection of the intermediate section 14, a deflection puller wire 44 passes through a third lumen 33. A position sensor cable assembly 48, including one or more single axis sensors (SAS) carried in the distal assembly 17, passes through a fourth lumen 34. To render an arcuate distal portion 15 of the distal assembly 17 variable in shape and size, e.g., curvature radii, in response to manipulation of the control handle by a user, a contraction wire 24 passes through a sixth lumen 36. As described below, the contraction wire 24 acts on an elongated shape-memory support member 50 that provides the 3-D shape of the distal assembly 17.

The multi-lumened tubing 23 of the intermediate section 14 is made of a suitable non-toxic material that is preferably more flexible than the catheter body 12. A suitable material is braided polyurethane or PEBAX, i.e., polyurethane or PEBAX with an embedded mesh of braided stainless steel or the like. The plurality and size of the lumens are not critical, provided there is sufficient room to house the relevant components. In the illustrated embodiment, the third and sixth lumens 33 and 36 for the deflection puller wire 44 and contraction wire 24 are off-axis and diametrically opposed to each other, and the fifth lumen 35 for the support member 50 is on-axis.

The useful length of the catheter, i.e., that portion that can be inserted into the body excluding the distal assembly 17, can vary as desired. Preferably the useful length ranges from about 110 cm to about 120 cm. The length of the intermediate section 14 is a relatively small portion of the useful length, and preferably ranges from about 3.5 cm to about 10 cm, more preferably from about 5 cm to about 6.5 cm.

Figure 5A:
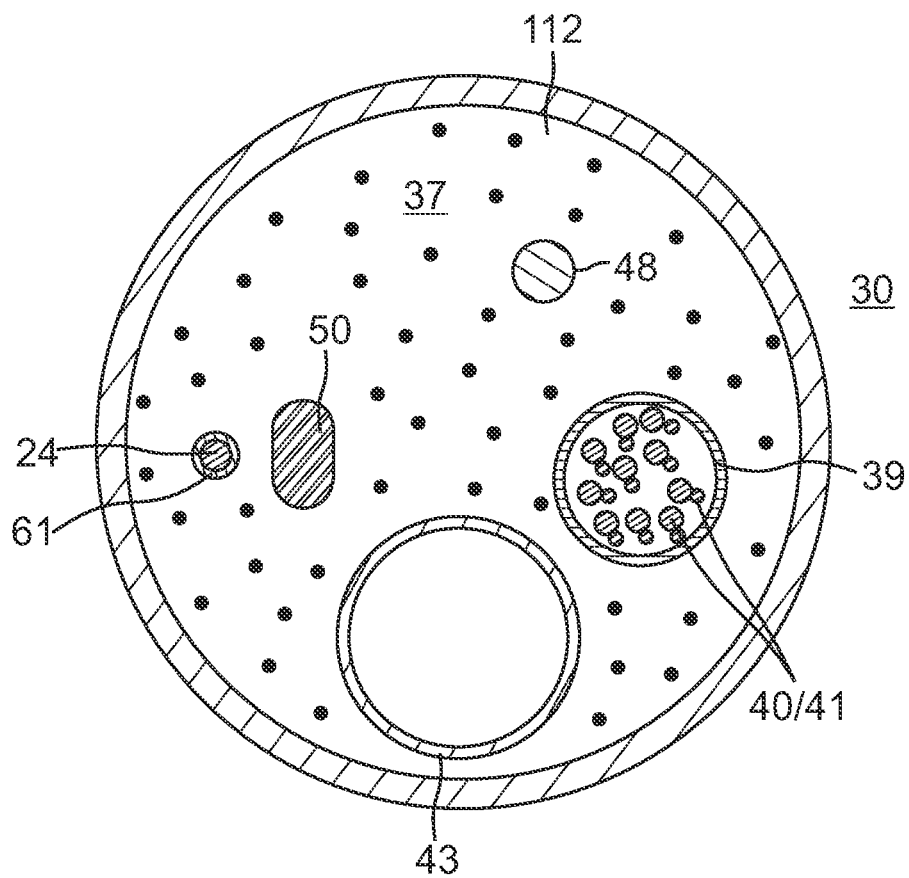
FIG. 5A is an end cross-sectional view of a connector section of the catheter of FIG. 1, taken along line C-C.
Figure 5B:
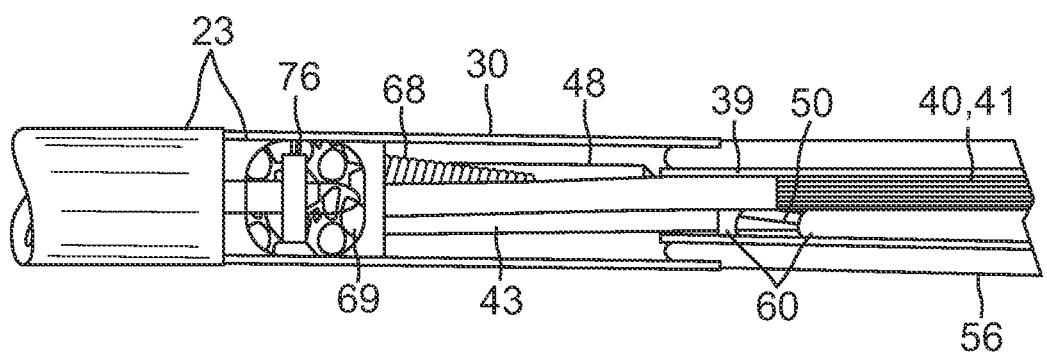
FIG. 5B is a side cross-sectional view of the connector section of FIG. 1, taken along area D-D.

Distal the intermediate section 14 is the distal assembly 17. Extending between the intermediate section 14 and the distal assembly 17 is a generally straight connector section 30, as shown in FIG. 2A and FIG. 5A, having a tubing of suitable material, e.g., PEEK, with a central lumen 37 that allows the various components extending between the intermediate section 14 and the distal assembly 17 to reorient and reposition as needed for transitioning therebetween, as shown in FIG. 5B. The components are potted in the lumen 37 of the connector section 30 by a suitable materials, for example, adhesive 112. Supporting the distal assembly 17 and providing its 3-D shape, the shape-memory support member 50 extends proximally from the distal assembly 17 for a relatively short distance into a distal portion of the connector section 30.

Figure 6A:
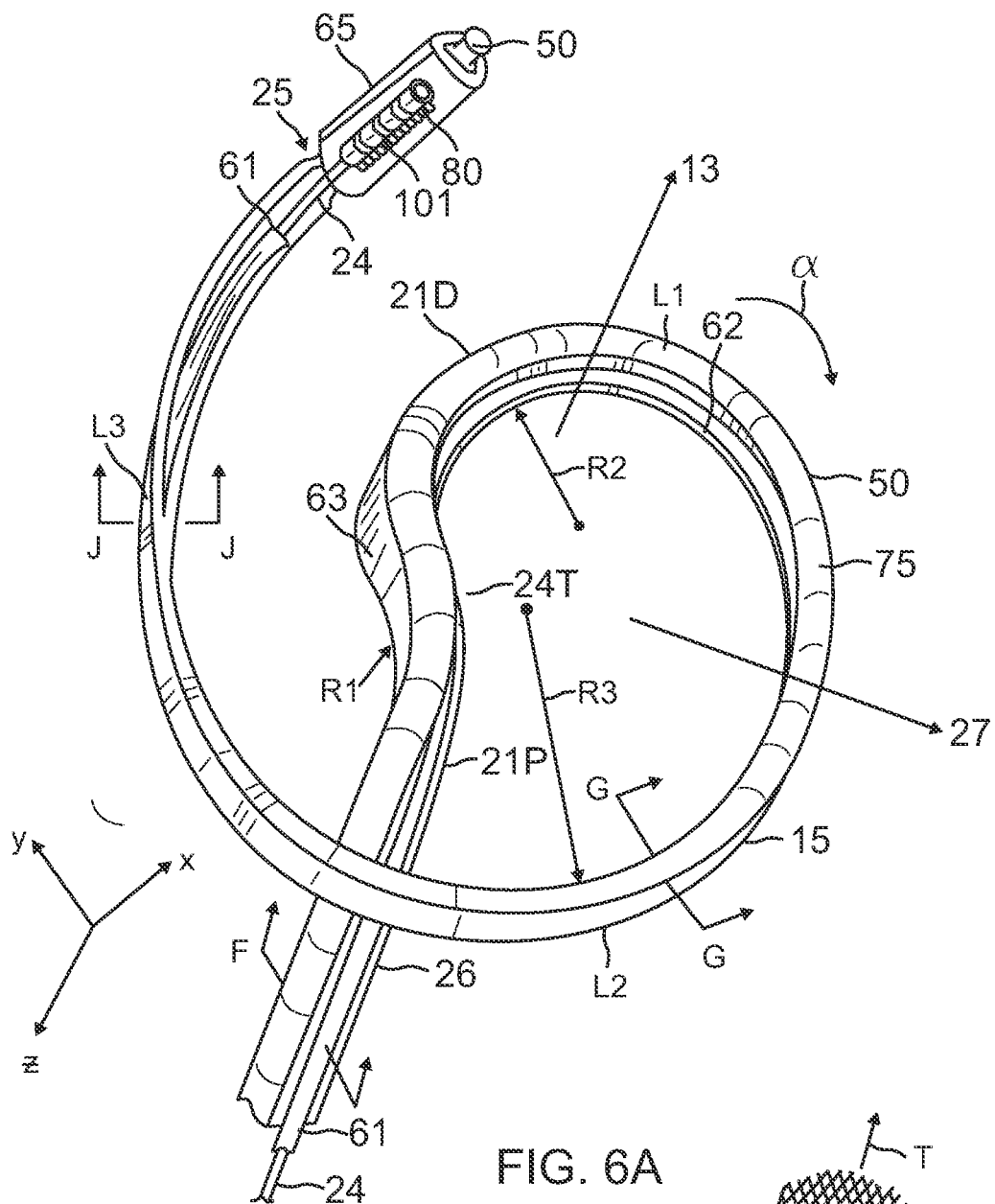
FIG. 6A is a perspective view of a support member and a coextensive contraction wire, along with a radially-constrictive tubing.
Figure 6D:
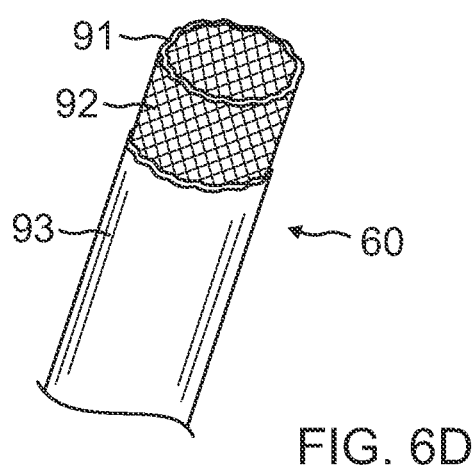
FIG. 6D is a perspective view of a radially-constrictive tubing, in accordance with another embodiment of the present invention.

As shown in FIG. 2A and FIG. 6, the 3-D distal assembly 17 includes a preformed, arcuate distal portion 15, an elbow portion 21, and a proximal linear stem 26. The arcuate distal portion 15 carries a plurality of irrigated ring electrodes 19. The elbow portion 21 is configured to orient the distal portion 15 obliquely to the longitudinal axis 13 such that the longitudinal axis extends generally through a center of the distal portion 15, as shown in FIG. 7. As such, an oblique angle θ (FIG. 2A) is defined between the longitudinal axis 13 and a plane P generally defined by the distal assembly 17, wherein the oblique angle θ ranges between about 45 degrees and 135, preferably about 75 and 100 degrees, and preferably about 90 degrees.

With reference to FIG. 2A, FIG. 6 and FIG. 7, the elbow portion 21 has a proximal curved section 21P, an elbow junction or "twist" 42, and a distal curved section 21D. The proximal curved section 21P traces a first arc defined by a first (or proximal) radius R1 relative to the longitudinal axis 13. The distal curved section 21D traces a second arc defined by a second (or mid) radius R2 relative to an axis 27 oblique to the longitudinal axis 13. The first radius R1 is lesser than the second radius R2. However, both radii R1 and R2 are lesser than a third (or distal) radius R3 defining a third arc traced by the distal portion 15. In some embodiments, the radius R1 ranges between about 0.1" and 0.25", the radius R2 ranges between about 0.15" and 0.38", and the radius R3 ranges between about 0.4" and 0.6". As such, the 3-D configuration of the distal assembly 17, when unconstrained, has a spiral characteristic, with radius R3 being greater than the radius R2. For example, where the oblique angle θ is about 90 degrees and the longitudinal axis 13 defines a Z axis, the first arc defined by radius R1 may lie in the Y/Z plane, and the second and third arcs defined respectively by radii R2 and R3 may both lie in the X/Y plane, as shown in FIG. 6. It is understood that the distal assembly 17 is not limited to the radii R1, R2 and R3 described above, and may contain more or less radii, as needed or desired.

The 3-D configuration of the distal assembly 17, when unconstrained, also has a helical characteristic in that the distal assembly 17 extends distally as it spirals such that the distal end 25 of the distal assembly 17 is the distal-most portion of the distal assembly 17, as best shown in FIG. 2A.

Accordingly, the distal assembly 17 has a spiral-helical configuration (or helical-spiral configuration) such that there are a first separation gap between the distal end 25 and the distal curved section 21D along the longitudinal axis 13, and a second separation gap between the distal end 25 and the distal curved section 21D along the oblique axis 27. The spiral-helical configuration of the distal assembly 17 can be described as tracing from its proximal end to its distal end an enlarging helix that is on-axis with the longitudinal axis, as shown in FIG. 2A.

Depending on the length of the distal portion 15, the distal assembly 17, in its neutral, unconstrained 3-D configuration, may subtend a radial angle α of about 360 degrees between the twist 42 and the distal end 25. In another embodiment, the distal assembly 17 subtends a radial angle α (FIG. 6) greater than 360 degrees, e.g., about 380 degrees. When the distal assembly 17 is contracted, as shown in FIG. 2B, the spiral-helical form "coils up" and tightens, with the one or more of radii R1, R2, R3 traced by the distal assembly 17 decreasing, and the radial angle α subtended by the distal assembly 17 increasing, for example, from about 360 or 380 degrees to about 540 degrees or more between the twist 42 and the distal end 25. Accordingly, the distal assembly 17 in its neutral, unconstrained configuration may be used for circumferential contact with an ostium having a larger radius, and then be adjusted into its contracted configuration for circumferential contact within the PV of the ostium with a significantly smaller radius.

Figure 8:
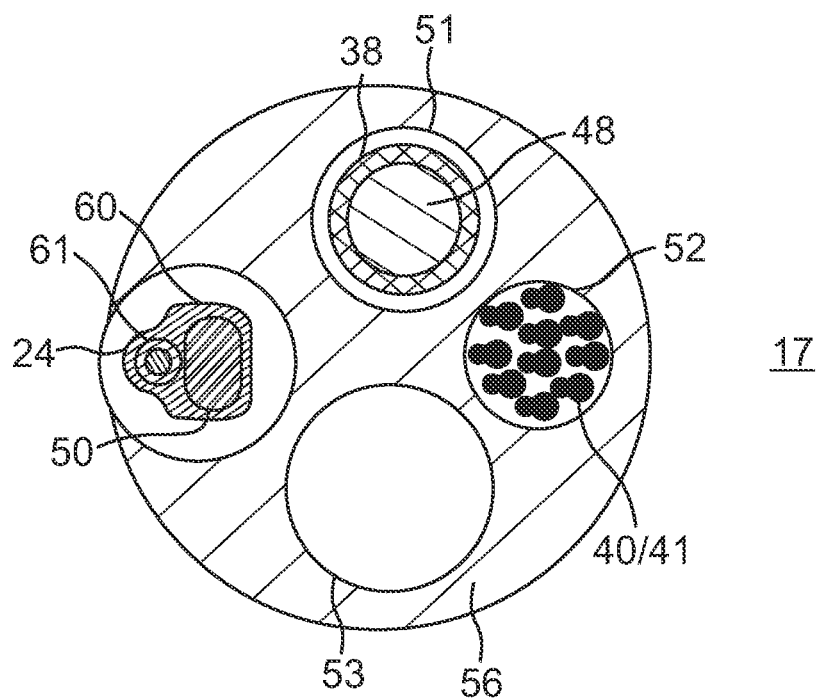
FIG. 8 is an end cross-sectional view of the distal assembly of FIG. 2A, taken along line E-E.

As shown in FIG. 8, the distal assembly 17 includes a multi-lumened tubing 56. In the disclosed embodiment, the tubing 56 has four off-axis lumens, namely, a first lumen 51 for the SAS cable assembly 48 (circumferentially surrounded by a friction-reducing coating 38, e.g., of TEFLON®), a second lumen 52 for the ring electrode wire pairs 40, 41, a third lumen 53 for irrigation fluid delivered through the irrigation tubing 43, and a fourth lumen 54 for the support member 50 and the contraction wire 24, a segment of which is coextensive with the support member 50 in the lumen 54. Again, position and sizing of the lumens are not critical, except the position of the fourth lumen 54 for the contraction wire 24 is preferably on or near an inner circumference of the spiral-helical form of the distal assembly 17 so that proximal movement of the wire 24 can act more effectively in tightening the spiral-helical form and increasing its coiling. The multi-lumened tubing 56 can be made of any suitable material, and is preferably made of a biocompatible plastic such as polyurethane or PEBAX.

In the depicted embodiment, the pre-formed support member 50 of the distal assembly 17 extends through the fourth lumen 54 of the tubing 56 to provide and define the 3-D spiral-helical shape of the distal assembly 17, which includes the twist 42 and arcs of the proximal section 21P and the distal section 21D, and the distal portion 15 defined by radii R1, R2 and R3. The support member 50 is made of a material having shape-memory, i.e., that can be straightened or bent out of its original shape upon exertion of a force and is capable of substantially returning to its original shape upon removal of the force. In some embodiments, a suitable material for the support member 50 is a nickel/titanium alloy. Such alloys typically comprise about 55% nickel and 45% titanium, but may comprise from about 54% to about 57% nickel with the balance being titanium. One nickel/titanium alloy is Nitinol, which has excellent shape memory, together with ductility, strength, corrosion resistance, electrical resistivity and temperature stability.

In some embodiments, as shown in FIG. 5A, the support member 50 has a proximal end received and affixed in the connector section 30 In some embodiments, the proximal end of the support member 50 extends at a depth of about 2-3 mm proximal of the distal end of the connector section 30. Alternatively, the support member 50 can extend further proximally into the lumen 35 of the intermediate section 14, through the entire length of the intermediate section 14, and even into the catheter body 12 via the central lumen 18, as desired or appropriate.

Advantageously, the support member 50 has a generally rectangular cross-sectional shape whose height and width dimensions vary in a predetermined manner along the length of the member 50. As shown in FIG. 13B and FIG. 13C, the generally rectangular cross-sectional area at any location along the length remains constant although its width dimension W and height dimension vary at different locations. There is no reduction or increase in the cross-sectional area at any location along the length in that any loss or gain in one dimension is proportionally gained or lost by the other dimension between a more proximal location and a more distal location along the length of the support member 50. As a tapered portion or "tail" of the support member 50 narrows in one dimension of the cross-sectional area from the proximal end to the distal end of the member, the other dimension of the cross-sectional area widens from the proximal end to the distal end. The dimension that decreases (for example, the width dimension W along the X axis in FIG. 13B and FIG. 13C) decreases its resistance to bending in that dimension from the proximal end to the distal end, while the dimension that increases (for example, the height dimension H along the Y axis in FIG. 13B and FIG. 13C) increases its resistance to bending in that dimension from a proximal end to a distal end of the tapered portion.

As shown in FIG. 6, the generally rectangular cross-section of the support member 50 at its proximal end has a maximum width W1 and a minimum height H1. For minimizing change or deformation in radii R1 and R2 during contraction of the distal assembly 17, the width and height dimensions of the cross-sectional area of the support member 50 begin to change (or taper) starting at a predetermined location distal of radius R2 (e.g., at or around location L2) Distal of the predetermined location, in the tapered tail of distal assembly 17, the width begins to decrease to W2 (<W1) while the height begins to increase to H2 (>H1). The width further decreases to W3 (<W2<W1) while the height further increases to H3 (>H2>H1) at distal location L3. These decreases and increases are smooth and continuous. This tapered configuration biases the support member 50 to have increasing less resistance to coiling toward the distal end 25 such as when contracted by the contraction wire 24, while providing increasingly more resistance to oblique forces toward the distal end 25 such as when the distal assembly 17 contacts tissue surface head on. Thus, this varied cross-sectional shape allows the distal assembly 17 to exhibit improved contraction characteristics, including the distal portion 15 being able to contract and coil readily with minimal deformation of the elbow junction 21 and the elbow junction 21 being better able to withstand the load from an axial force that is applied when the distal assembly 17 comes into contact with target tissue. With this varied cross-sectional shape applied to the support member 50, the distal assembly 17 can be adjusted, upon actuation of the contraction wire 24, to assume a smaller loop size (see FIG. 2B), for example, where the distal portion 15 assumes a curvature that is generally equal to or even be lesser than the curvature of the distal section 21D.

As shown in FIG. 6, with a generally rectangular cross-section, the support member 50 resembles a "coiled ribbon" having sides/surfaces 62 and 63 defining a height dimension of the generally rectangular cross-section, and edges 75 defining a width dimension of the generally rectangular cross-section. Advantageously, the inner flat side/surface 62, along its length, continually faces the inner circumference of the spiral-helical configuration of the distal assembly, and an outer flat side/surface 63 that is opposite of the inner flat surface 62 continually faces outwardly, away from the inner circumference of the spiral-helical configuration. The tapering of the support member 50 results in the "tapered tail" of the distal assembly 17 resembling an increasing wider and thinner ribbon.

Figure 4:
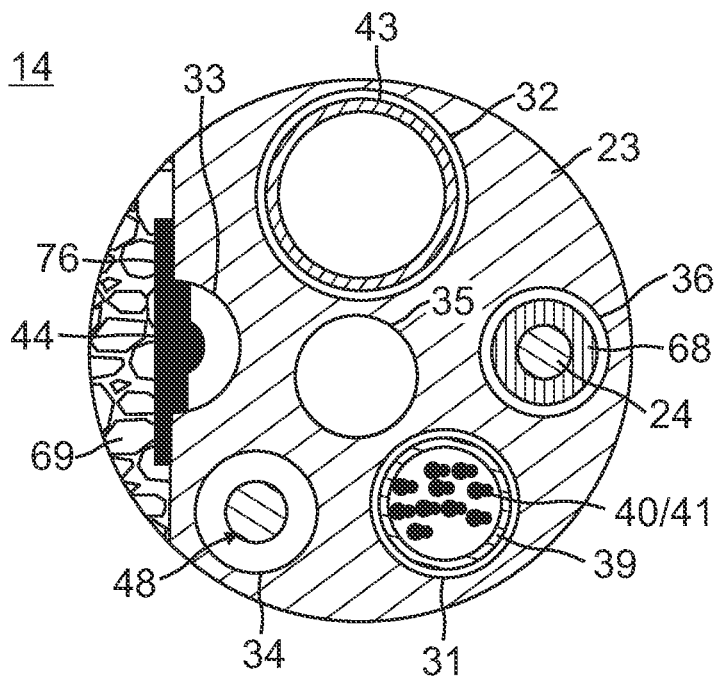
FIG. 4 is an end cross-sectional view of a deflectable intermediate section of the catheter of FIG. 1, taken along line B-B.

Moreover, the generally rectangular cross-section at the proximal end of the support member 50 helps anchor the proximal end in the lumen 35 of the tubing 23 of the deflectable section 14 and reduces the risk of the support member rotating about its axis where the proximal end is potted by an adhesive, e.g., epoxy (see FIG. 4).

In some embodiments, the support member 50 begins with a round cross-sectional shape, as shown in FIG. 13A. The support member 50, for example, a round wire, is progressively flattened to produce the generally rectangular cross-section and tapered tail. Thus, the two opposed ends of the width dimension between the parallel fattened surfaces of the height dimension carry the residual round shape of the original round cross-sectional shape. It is understood that the support member may begin with a square/rectangular cross-sectional shape which would then result in flat opposed ends instead of round opposed ends. In some embodiments, using a round wire may be more economical to manufacture, and rounded opposed ends may ease the assembly of the distal assembly 17, including insertion of the support member into a radially-constrictive flexible tubing or sleeve 60, as discussed further below. The rounded opposed ends may reduce the insertion force used to insert the support member 50 into the tubing 60 and also the risk of the support member 50 tearing and damaging the tubing 60.

In some embodiments, the support member 50, as a round wire, has an initial (pre-flattening) diameter of about 0.019 inches and a length of about 4.25 inches. When flattened, the support member 50 has a generally rectangular cross-sectional dimensions of about 0.021"×0.015" from its proximal end to the location L2. The tapered tail of the support member 50 (distal of location L2 in FIG. 6) is about 2.9 inches long and has a generally rectangular cross-sectional dimensions of about 0.035"×0.008" at or near its distal end 25. In some embodiments, a distal end of the support member 50 has an unflattened section 50D which retains its round cross-section, as explained below in further detail.

The area moment of inertia for the 0.019 inch diameter support member 50 (pre-flattening) is the same regardless of centroidal axis orientation, whereas the area moment of inertia at or near its distal end for the first centroidal axis is 2.5 times less stiff than the moment of inertia at the proximal end. The moment of inertia for the second centroidal axis at the distal end is 4.5 times stiffer than the moment of inertia at the proximal end. Comparing the two centroidal axis area moments of inertia at the distal end with respect to each other, the first centroidal axis is 18.5 times less stiff than the second centroidal axis. Since the contraction wire 24 exerts a constant inwardly line of force (neglecting friction) on the support member 50, to obtain a small, generally circular contraction, the area moment of inertia of the support member 50 should constantly decrease towards the distal end where it is attached to the contraction wire 24.

Figure 9:
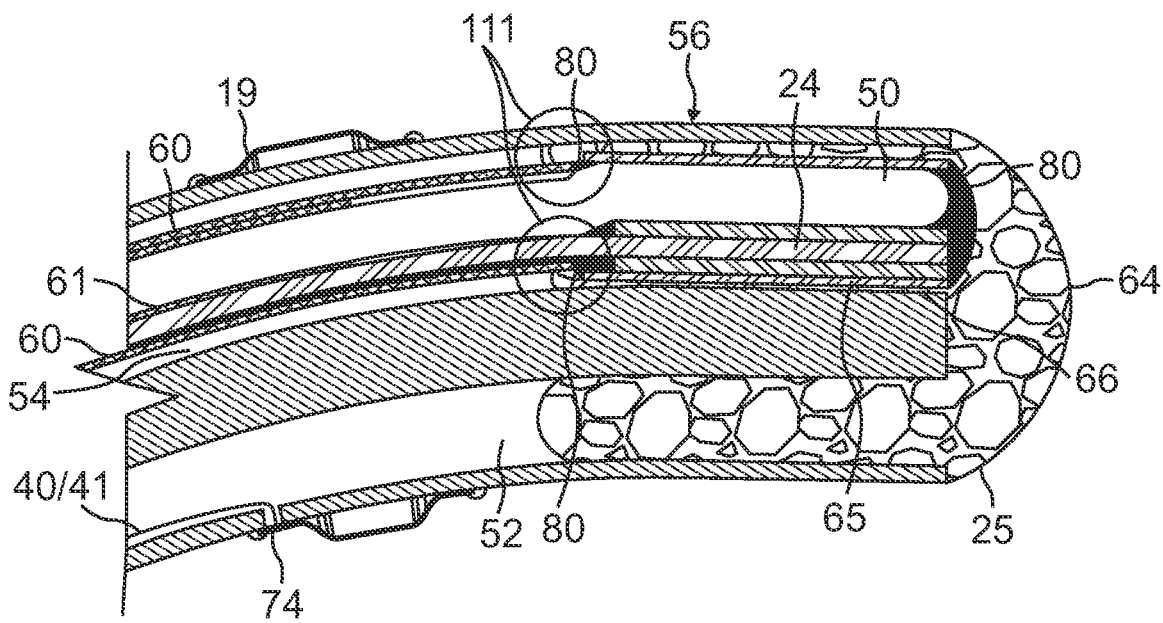
FIG. 9 is a side cross-sectional view of the distal assembly of FIG. 2A, taken along line F-F.

The contraction wire 24 has a proximal end anchored in the control handle 16 which provides a rotational control knob 59 (see FIG. 1) for actuating the contraction wire 24 via manipulation by an operator. The contraction wire 24 extends through the central lumen 18 of the catheter body 12 (FIG. 3), the sixth lumen 36 of the intermediate section 14 (FIG. 4), the central lumen 37 of the connector section 30 (FIG. 5A) and the fourth lumen 54 of the tubing 56 of the distal assembly 17 (FIG. 8) alongside the support member 50, to the distal end 25 (FIG. 9).

The contraction wire 24 may be covered by a friction-reducing tubing 61 (FIG. 8), e.g., a TEFLON® coated inner diameter of a polyimide or PEEK tubing, so that the contraction wire 24 is physically separated and isolated from the side 62 of the support member 50 and the inside surface of the constrictive tubing 60 that surrounds the contraction wire 24 and the support member 50, which is described below in further detail. The friction-reducing tubing 61 may have a proximal end in the connector section 30 and a distal end at least distal of the radius R2, at or near the location L2, if not closer to the distal end of the support member 50.

Advantageously, the support member 50 and the coextensive segment of the contraction wire 24 (and its tubing 61) through the lumen 54 of the distal assembly 17 are surrounded and bound together by the tight-fitting flexible tubing 60.

Figure 6C:
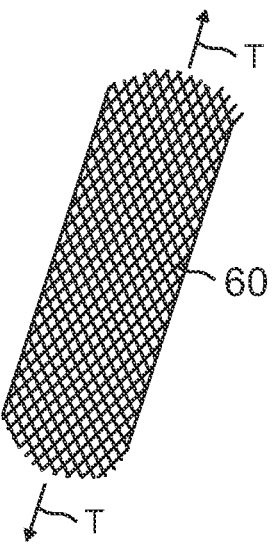
FIG. 6C is a perspective view of a radially-constrictive tubing, in accordance with an embodiment of the present invention.
Figure 6B:
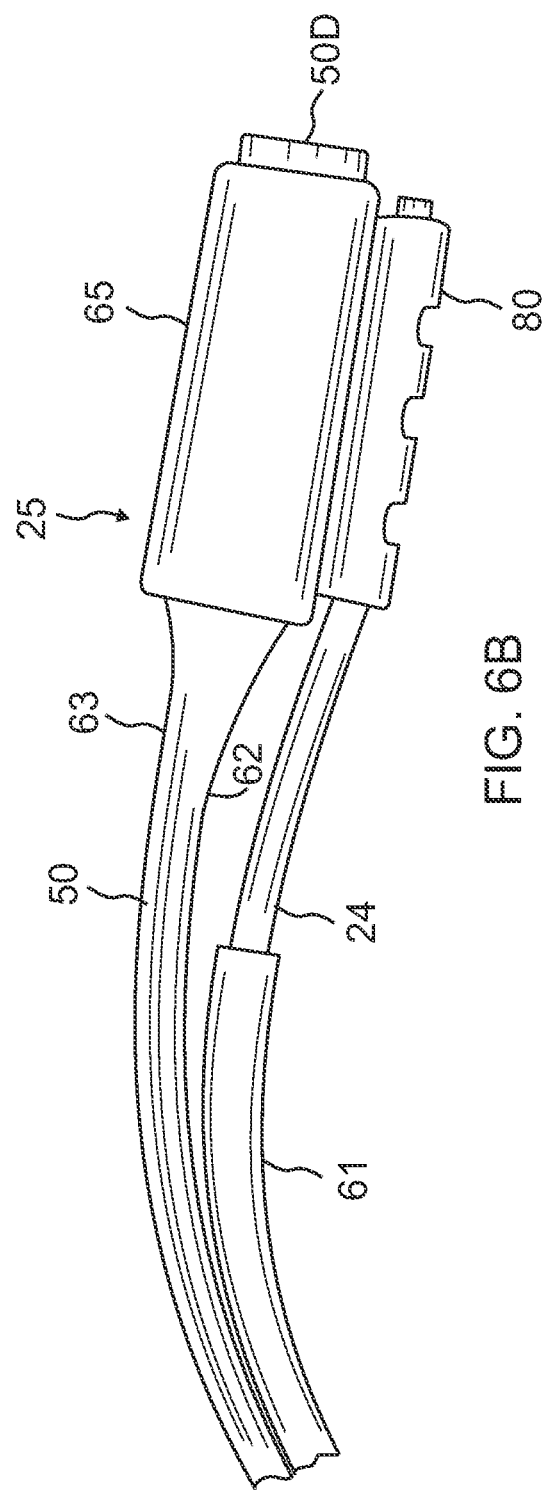
FIG. 6B is a detailed top view of an assembled structure of distal ends of the support member and the contraction wire of FIG. 6A.
Figure 7:
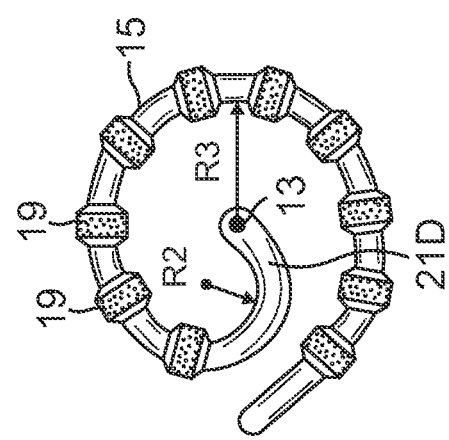
FIG. 7 is an end view of the distal assembly of FIG. 1.

In some embodiments, as shown in FIG. 6C, the tubing 60 to provide radial constriction includes a woven or braided tubing of a manufactured fiber, spun from a liquid crystal polymer (LCP), for example, manufactured fiber sold under the trademark VECTRAN®. Chemically, it is an aromatic polyester produced by the polycondensation of 4-hydroxybenzoic acid and 6-hydroxynaphthalene-2-carboxylic acid. These fibers exhibit thermal stability at high temperatures, high strength and modulus, low creep and good chemical stability.

The resulting tubing has a high modulus of elasticity which allows for improved contraction of the distal assembly 17. In some embodiments, the manufactured fiber is braided at high pix per inch (PPI) of about 128 and is free of resin so that there is little restriction on the bending radius of the tubing. A tubing of such manufacture satisfies the strength required to constrain the contraction wire 24 from tearing the sidewall of the tubing 56. Moreover, the tubing is sufficiently flexible to allow contraction of the distal assembly 17, and sufficiently strong to withstand frictional fatigue of the contraction wire 24 and other moving components imposed on the tubing fibers.

In some embodiments, after the tubing 60 has been slipped onto the support member 50 and the contraction wire 24, tension force T is applied to its ends to lengthen longitudinally and shorten radially to provide a radially constrictive tight fit around the support member 50 and the contraction wire 24 in ensuring that the contraction wire 24 remains in the proper location relative to the support member 50, thus ensuring that the pulling force vector is in alignment with the support member 50 for a more efficient loop contraction and improved loop contraction geometry. The tubing 60 may also be fused to the lumen 54.

In other embodiments, as shown in FIG. 6D, the tubing 60 for radial constriction has an inner diameter 91 composed of a friction-reducing material, such as, TEFLON®, (formed as a first extrusion coat or layer), which is covered by a stainless steel flat braid 92, which is covered by an outer diameter 93, such as nylon (formed as a second extrusion coat or layer). The constrictive tubing 60 is slipped over the support member 50 and the contraction wire 24 (with its friction-reducing tubing 61) after their distal ends are affixed together, as described further below.

In some embodiments, the constrictive tubing 60 has a distal end at or near a junction of the radii R2 and R3, and a proximal end at or near the elbow junction 21. The constrictive tubing 60 is fitted to provide circumferential/radial constriction around the member 50, the contraction wire 24 with its friction-reducing tubing 61 (see FIG. 8) so as to secure the tubing 61 against the inner side 62 of the support member 50 in keeping the contraction wire 24 aligned with (or on the side of) the inner side 62 for improving contraction characteristics of the distal assembly 17, including improved circular shape maintenance and significantly tighter contraction and coiling, as well as improved durability against the contraction wire 24 cutting into the tubing 56 of the distal assembly 17.

Such improved contraction characteristics, particularly of the tapered tail of the distal assembly, is enabled by keeping the contraction 24 against the inner side 62 throughout the length of the support member 50. For example, where a radius R3 of the arc of distal portion 15 is about 17 mm when the distal assembly 17 is unconstrained, the distal assembly 17 can be contracted into a tighter coil such that the arcs of the distal curve portion 21D and the distal portion 15 are both defined by a radius of about 10 mm, for a reduction in the radius R3 of the arc of the distal portion 15 by about 60% or more.

As illustrated in FIG. 6, the contraction wire 24 within its tubing 61 runs along the entire length of the inner-facing side 62 of the support member 50 extending between the distal end 25 of the distal assembly 17 and the connector section 30. This predetermined pattern advantageously minimizes any tendency for the contraction wire 24 to separate and lift from the support member 50 when the contraction wire 24 is drawn proximally. In some embodiments, the contraction wire 24 may also have a rectangular cross-section along its length or along one or more segments thereof.

With reference to FIG. 8 and FIG. 9, an assembled structure of the distal ends of the support member 50, contraction wire 24 and constrictive tubing 60 is oriented within the fourth lumen 54 of the tubing 56 of the distal assembly 17 such that the contraction wire 24 is most adjacent to the inner circumference of the distal assembly 17 to face the center of the distal assembly 17. With the fourth lumen 54 positioned closer to the inner circumference than the other lumens of the tubing 56, and the contraction wire 24 within the lumen 54 also positioned closer to the inner circumference than the support member 50, the contraction wire 24 can effectively contract the distal assembly 17.

Prior to insertion into the lumen 54, the assembled structure of the distal ends of the support member 50, the contraction wire 24 and the constrictive tubing 60 is prepared. In some embodiments, a coupling of the distal ends of the contraction wire 24 and support member 50 includes a laser welded coupling having a stainless steel ferrule 65 (e.g., 304 or 316 series) that is placed over the distal end 25D of the support member 50 which is not flattened but retains its original round cross-sectional shape. The ferrule 65 is flattened after it is placed over the distal end 25D. The flattened portion of the support member 50 acts as a stop preventing any proximal migration or dislocation of the ferrule 65 when contraction wire tension is applied to the support member 50. The ferrule 65 is secured to the round distal end 50D of the support member 50 by a crimp die which has a flat portion that is clocked parallel to the surface 62 of the support member 50. The distal end of the contraction wire 24 has a crimped ferrule 80 which has a flat portion that is also fixed to the flat portion of the ferrule 65. A laser seam weld 101 is made on one common (bottom) side of the ferrules 65 and 80 joining the distal ends of the contraction wire 24 and the support member 50.

In contrast to prior art coupling of the support member and the contraction wire which used lead-free solder to join a nitinol support member to the contraction wire, the laser welded coupling described herein includes the use of strong acid flux to remove oxides from the nitinol and stainless steel before soldering. Moreover, the laser welded coupling provides a much stronger attachment compared to the prior art the lead-free solder with a low shear and tensile strength (about 4000 psi) which can attribute to puller wire detachment failures from the nitinol support member when the lead-free solder contained unexposed voids or was formed as a cold solder joint.

The constrictive tubing 60 is then slid over the contraction wire 24 at its proximal end, advanced over the support member 50 at its proximal end, and further advanced until the distal end of the tubing 60 reaches and covers the assembled structure.

When the constrictive tubing 60 has been properly positioned over the contraction wire 24 and the support member 50, the constrictive tubing 60 has a proximal end near a junction of radii R2 and R3, and it distal end is trimmed or otherwise provided with a finished distal end terminating immediately proximal of the stainless steel ferrule 65. The finished distal end of the constrictive tubing 60 is then affixed to the friction-reducing tubing 61 and the support member 50 by a circumferential application of an adhesive 111, e.g., LOCTITE®. Notably, the friction-reducing tubing 61 surrounding the contraction wire 24 has a distal end that is well proximal of the soldered stainless steel ferrule 65 so that the adhesive 111 can bond the distal end of the constrictive tubing 60 directly on to the contraction wire 24 and the support member 50.

The assembled structure of the contraction wire 24, the support member 50 and the constrictive tubing 60 is then inserted into the lumen 54, where the stainless steel ferrule 65 and its contained components are fixed and anchored at the distal end of the multi-lumened tubing 56 by an adhesive 64, e.g., polyurethane, which covers the entire distal face of the distal end 25 to form a tip dome, as shown in FIG. 9. With this arrangement, the relative positions of the contraction wire 24 and the support member 50 can be controlled so that the contraction wire 24 is positioned on or near the inner circumference of the distal assembly 17, closer to the center of the spiral-helical form, as described above. The constrictive tubing 60 protects the multi-lumened tubing 56 from the contraction wire 24 cutting into its side wall during contraction of the distal assembly 17.

With reference to FIG. 3 and FIG. 4, a compression coil 68 surrounding the contraction wire 24 extends from the proximal end of the catheter body 12 and through the entire length of the sixth lumen 36 of the intermediate section 14. Thus, the compression coil has a distal end at or near a mid-location in the connector section 30. The compression coil 68 is made of any suitable metal, preferably stainless steel, and is tightly wound on itself to provide flexibility, i.e., bending, but to resist compression. The inner diameter of the compression coil is preferably slightly larger than the diameter of the contraction wire 24. The outer surface of the compression coil is covered by a flexible, non-conductive sheath 67, e.g., made of polyimide tubing. The compression coil preferably is formed of a wire having a square or rectangular cross-sectional area, which makes it less compressible than a compression coil formed from a wire having a circular cross-sectional area. As a result, the compression coil 68 keeps the catheter body 12, and particularly the intermediate section 14, from deflecting when the contraction wire 24 is drawn proximally to contract the distal assembly 17, as the compression coil 68 absorbs more of the compression.

Figure 10:
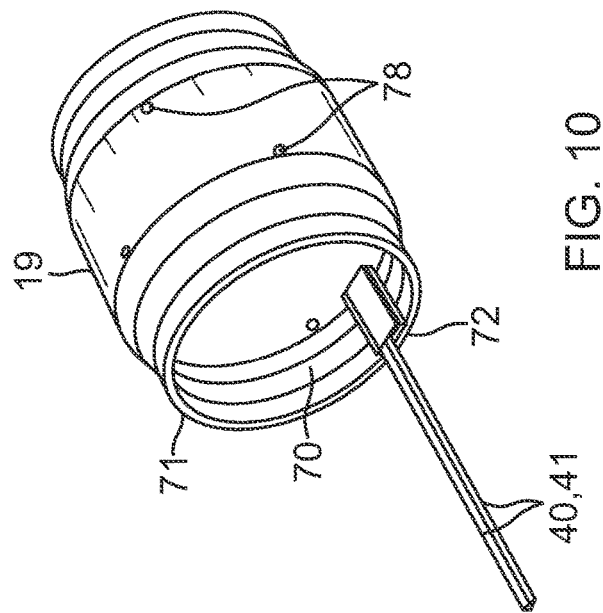
FIG. 10 is a perspective view of an irrigated ablation electrode with lead wire attachments, according to one embodiment.

The ring electrodes 19 are mounted on predetermined locations on the distal portion 15, as shown in FIG. 2A and FIG. 2B. The electrodes can be made of any suitable solid conductive material, such as platinum or gold, preferably a combination of platinum and iridium or gold and platinum, and mounted onto the tubing with glue or the like. A suitable embodiment of an electrode adapted for ablation and irrigation is illustrated in FIG. 10. An ablation reservoir ("AR") electrode is generally cylindrical with a length greater than its diameter. In one embodiment, the length is about 3.0 mm, the outer diameter is about 2.8 mm, and the inner diameter is about 2.33 mm.

In some embodiments, the plurality of AR ring electrodes 19 on the distal assembly 17 can ranges from about six to about twenty, more preferably from about eight to about twelve. In some embodiments, the distal assembly 17 carries ten AR electrodes. The electrodes can be approximately evenly spaced along the distal portion 15.

The proximal end of each wire of the wire pairs 40, 41 is electrically connected to a suitable connector (not shown) distal of the control handle 16. In the disclosed embodiment, wire 40 of a wire pair is a copper wire, e.g. a number "40" copper wire, and the other wire 41 of the wire pair is a constantan wire. The wire pairs extend from the control handle 16, through the central lumen 18 of the catheter body 12 (FIG. 3), the first lumen 31 of the intermediate section 14 (FIG. 4), the central lumen 37 of the connector section 30 (FIG. 5A), and the second lumen 52 of the distal assembly 17 (FIG. 8). The distal ends of the wire pairs pass through holes 74 (FIG. 9) formed in the side wall of the tubing 56 to reach the AR electrodes 19. The wires of each pair are electrically isolated from each other except at their distal ends where they are exposed. Exposed distal ends of a respective wire pair 40, 41 are sandblasted, and wrapped in and welded to a folded metal foil 72 (e.g., copper foil) which is then welded to an inner surface 70 near a proximal end 71 of its AR electrode 19, as shown in FIG. 10.

Ablation energy, e.g., RF energy, is delivered to the AR electrodes 19 via the wire 40 of the wire pairs. However, the wire pairs inclusive of their respective constantan wire 41 can also function as temperature sensors or thermocouples sensing temperature of each AR electrode 19.

All of the wire pairs pass through one nonconductive protective sheath 39 (FIG. 3 and FIG. 4), which can be made of any suitable material, e.g., polyimide, in surrounding relationship therewith. The sheath 39 extends with the wire pairs from the control handle 16, the catheter body 12, the intermediate section 14, the connector section 30 and into the second lumen 52 of the distal assembly 17, terminating just distal of the junction between the connector section 30 and the distal assembly 17, for example, about 5 mm into the second lumen 52. The distal end is anchored in the second lumen 52 by glue, for example, polyurethane glue or the like.

Irrigation fluid is delivered to the distal assembly by the irrigation tubing 43 whose proximal end is attached to a luer hub 73 (FIG. 1) proximal of the control handle 16 and receives fluid delivered by a pump (not shown). The irrigation tubing 43 extends through the control handle 16, the central lumen 18 of the catheter body 12 (FIG. 3), the second lumen 32 of the intermediate section 14 (FIG. 4), the central lumen 37 of the connector section 30 (FIG. 5A) and a short distance, e.g., about 5 mm, distally into the third lumen 53 of the multi-lumened tubing 56 of the distal assembly 17. The fluid enters the third lumen 53 where it exits via openings (not shown) formed in the sidewall of the tubing 56 to enter the AR ring electrodes 19 and exits apertures 78 formed in the electrode side wall (FIG. 10). It is understood that the distal portion 15 may carry any form of electrodes, including the aforementioned AR ring electrodes, impedance ring electrodes, and/or combinations thereof, as desired or appropriate.

The deflection puller wire 44 is provided for deflection of the intermediate shaft 14. The deflection wire 44 extends through the central lumen 18 of the catheter body 12 (FIG. 3) and the third lumen 33 of the intermediate section 14 (FIG. 4). It is anchored at its proximal end in the control handle 16, and at its distal end to a location at or near the distal end of the intermediate section 14 by a T-bar 76 (FIG. 4) that is affixed to the sidewall of the tubing 15 by suitable material, e.g., polyurethane 69. The puller wire 54 is made of any suitable metal, such as stainless steel or Nitinol, and is preferably coated with TEFLON® or the like. The coating imparts lubricity to the puller wire. The puller wire 44 may have a diameter ranging from about 0.006 to about 0.010 inch.

A second compression coil 47 is situated within the central lumen 18 of the catheter body 12 in surrounding relation to the puller wire 44 (FIG. 3). The second compression coil 47 extends from the proximal end of the catheter body 12 to at or near the proximal end of the intermediate section 14. The second compression coil 47 is made of any suitable metal, preferably stainless steel, and is tightly wound on itself to provide flexibility, i.e., bending, but to resist compression. The inner diameter of the second compression coil 47 is preferably slightly larger than the diameter of the puller wire 44. A TEFLON® coating (not shown) on the puller wire allows it to slide freely within the second compression coil. Within the catheter body 12, the outer surface of the second compression coil 47 is covered by a flexible, non-conductive sheath 49, e.g., made of polyimide tubing. The second compression coil 47 is anchored at its proximal end to the outer wall 20 of the catheter body 12 by a proximal glue joint and to the intermediate section 14 by a distal glue joint.

Within the third lumen 33 of the intermediate section 14, the puller wire 44 extends through a plastic sheath (not shown), preferably of TEFLON®, which prevents the puller wire 44 from cutting into the wall of the tubing 23 of the intermediate section 14 when the intermediate section 14 is deflected.

Longitudinal movement of the contraction wire 24 relative to the catheter body 12, which results in contraction of the spiral-helical form of the distal assembly 17, is accomplished by suitable manipulation of the control handle 16. Similarly, longitudinal movement of the deflection wire 44 relative to the catheter body 12, which results in deflection of the intermediate section 14, is accomplished by suitable manipulation of the control handle 16. Suitable control handles for manipulating more than one wire are described, for example, in U.S. Pat. Nos. 6,468,260, 6,500,167, and 6,522,933, the entire disclosures of which are incorporated herein by reference.

Figure 11:
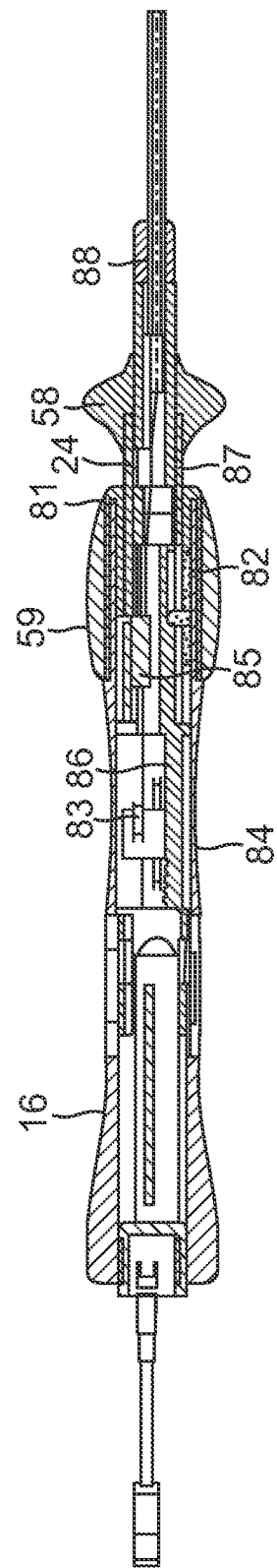
FIG. 11 is a side cross-sectional view of a control handle, in accordance with one embodiment.
Figure 12:
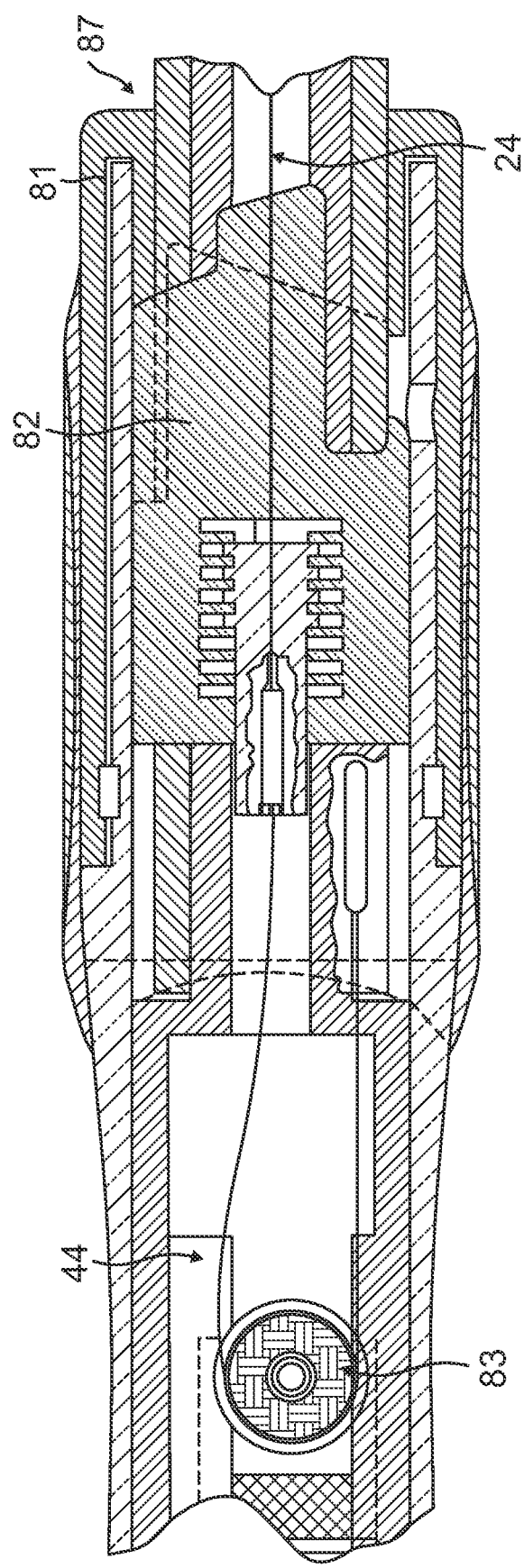
FIG. 12 is a partial top cross-sectional view of the control handle of FIG. 11.

In one embodiment, the catheter includes a control handle 16 as shown in FIG. 11 and FIG. 12. The control handle 16 includes a deflection control assembly that has a handle body 84 in which a core 86 is fixedly mounted and a piston 87 is slidably mounted over a distal region of the core 86. The piston 87 has a distal portion that extends outside the handle body. A thumb knob 58 is mounted on the distal portion so that the user can more easily move the piston 87 longitudinally relative to the core 86 and handle body 84. The proximal end of the catheter body 12 is fixedly mounted to the distal end of the piston 87. An axial passage 88 is provided at the distal end of the piston 87, so that various components, including lead wires 40, 41, contraction wire 24, deflection wire 44, position sensing cable assembly 48 and irrigation tubing 43 that extend through the catheter body 12 can pass into the control handle. The lead wires 40, 41 can extend out the proximal end of the control handle 16 or can be connected to a connector that is incorporated into the control handle, as is generally known in the art. The irrigation tubing 43 can also extend out the proximal end of the control 16 for connection with an irrigation source (not shown) via a luer hub.

The proximal end of the deflection wire 44 enters the control handle 16, and is wrapped around a pulley 83 and anchored to the core 86. Longitudinal movement of the thumb knob 58 and piston 87 distally relative to the handle body 84 and core 86 draws the proximal end of the deflection wire 44 distally. As a result, the deflection wire 44 pulls on the side of the intermediate section 14 to which it is anchored, thereby deflecting the intermediate section in that direction. To release and straighten the intermediate section 14, the thumb knob 58 is moved proximally which results in the piston 87 being moved proximally back to its original position relative to the handle body 84 and core 86.

The control handle 16 is also used for longitudinal movement of the contraction wire 24 via a rotational control assembly. In the illustrated embodiment, the rotational control assembly includes a cam handle 81 and a cam receiver 82. By rotating the cam handle in one direction, the cam receiver is drawn proximally to draw on the contraction wire 24. By rotating the cam handle in the other direction, the cam receiver is advanced distally to release the contraction wire 24. The contraction wire 24 extends from the catheter body 12 into the control handle 16, through the axial passage in the piston 88 and through the core 86 to be anchored in an adjuster 85 by which tension on the contraction wire can be adjusted.

In one embodiment, the position sensor cable assembly 48 including a plurality of single axis sensors ("SAS") extends through the first lumen 51 of the distal assembly 17 (FIG. 8), where each SAS occupies a known or predetermined position on the spiral-helical form of the distal assembly 17. The cable assembly 48 extends proximally from the distal assembly 17 through the central lumen 37 of the connector section 30, the fourth lumen 34 of the intermediate section 14 (FIG. 4), the central lumen 18 of the catheter body 12 (FIG. 3), and into the control handle 16. Each SAS can be positioned with a known and equal spacing separating adjacent SASs. In the disclosed embodiment, the cable carries three SASs that are positioned under the distal-most AR electrode, the proximal-most AR electrode, and a mid AR electrode, for sensing location and/or position of the distal assembly 17. The SASs enable the spiral-helical form to be viewed under mapping systems manufactured and sold by Biosense Webster, Inc., including the CARTO, CARTO XP and NOGA mapping systems. Suitable SASs are described in U.S. Pat. No. 8,792,962, the entire disclosure of which is incorporated herein by reference.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:
1. An electrophysiology catheter comprising:
   an elongated catheter body;
   a contraction wire having a proximal end and a distal end; and
   a distal assembly configured for contraction by actuation of the contraction wire, the distal assembly comprising:
      a plurality of ablation-reservoir electrodes, each including a side wall and an exit aperture disposed through the side wall; and a shape-memory support member comprising:
- a proximal generally rectangular portion comprising a first flat side having a first height and a first rounded side having a first width,
- an intermediate generally rectangular portion distal of the proximal generally rectangular portion comprising a second flat side having a second height that is greater than the first height and a second rounded side having a width that is less than the first width,
- a distal generally rectangular portion distal of the intermediate generally rectangular portion comprising a third flat side having a third height that is greater than the second height and a third rounded side having a third width that is less than the second width, the distal generally rectangular portion being coupled to the distal end of the contraction wire by a laser weld, and
- a distal end distal of the distal generally rectangular portion having a round cross section.

2. The electrophysiology catheter of claim 1, in which the plurality of ablation-reservoir electrodes comprise from six to twenty ablation-reservoir electrodes.

3. The electrophysiology catheter of claim 2, in which the plurality of ablation-reservoir electrodes are evenly spaced along the distal assembly.

4. The electrophysiology catheter of claim 2, in which the plurality of ablation-reservoir electrodes comprise from eight to twelve ablation-reservoir electrodes.

5. The electrophysiology catheter of claim 2, in which the plurality of ablation-reservoir electrodes each have a length greater than an outer diameter.

6. The electrophysiology catheter of claim 5, in which the length is 3.0 mm and the outer diameter is 2.8 mm.

7. The electrophysiology catheter of claim 2, in which the distal assembly further comprises a radially-constrictive tubing that surrounds the shape-memory support member and a coextensive portion of the contraction wire.

8. The electrophysiology catheter of claim 7, in which the radially-constrictive tubing includes fibers formed from a liquid crystal polymer.

9. The catheter of claim 8, in which the fibers are woven such that the radially-constrictive tubing has a woven construction.

10. The catheter of claim 8, wherein the fibers are braided such that the radially-constrictive tubing has a braided construction.

11. The catheter of claim 10, wherein the braided construction is braided at about 128 PPI.

12. An electrophysiology catheter comprising:
an elongated catheter body;
a contraction wire having a proximal end and a distal end; and
a distal assembly configured for contraction by actuation of the contraction wire, the distal assembly including a support member comprising:
- a proximal generally rectangular portion comprising a first flat side having a first height and a first rounded side having a first width,
- an intermediate generally rectangular portion distal of the proximal generally rectangular portion comprising a second flat side having a second height that is greater than the first height and a second rounded side having a width that is less than the first width,
- a distal generally rectangular portion distal of the intermediate generally rectangular portion comprising a third flat side having a third height that is greater than the second height and a third rounded side having a third width that is less than the second width, the distal generally rectangular portion being coupled to the distal end of the contraction wire by a laser weld, and
- a distal end distal of the distal generally rectangular portion having a round cross section.

13. The electrophysiology catheter of claim 12, in which the distal assembly further comprises a plurality of ablation-reservoir electrodes, each including a side wall and an exit aperture disposed through the side wall.

14. The electrophysiology catheter of claim 13, in which the plurality of ablation-reservoir electrodes each have a length greater than an outer diameter.

15. The electrophysiology catheter of claim 14, in which the distal assembly further comprises a radially-constrictive tubing that surrounds the support member and a coextensive portion of the contraction wire.

16. The electrophysiology catheter of claim 15, in which the radially-constrictive tubing includes fibers formed from a liquid crystal polymer.

17. The electrophysiology catheter of claim 16, in which the plurality of ablation-reservoir electrodes comprise from six to twenty ablation-reservoir electrodes.

18. The electrophysiology catheter of claim 17, in which the plurality of ablation-reservoir electrodes are evenly spaced along the distal assembly.

19. The electrophysiology catheter of claim 18, in which the plurality of ablation-reservoir electrodes comprise from eight to twelve ablation-reservoir electrodes.

* * * * *